United States Patent
Iwai et al.

(10) Patent No.: US 11,278,489 B2
(45) Date of Patent: Mar. 22, 2022

(54) COSMETIC COMPOSITION FOR NAILS, METHOD OF USING SAME, AND COSMETIC RESIN FOR NAILS

(71) Applicant: MENICON CO., LTD, Nagoya (JP)

(72) Inventors: Kaoru Iwai, Kasugai (JP); Masaki Baba, Kasugai (JP)

(73) Assignee: MENICON CO., LTD., Nagoya (JP)

( * ) Notice: Subject to any disclaimer, the term of this patent is extended or adjusted under 35 U.S.C. 154(b) by 0 days.

(21) Appl. No.: 16/335,983

(22) PCT Filed: Sep. 25, 2017

(86) PCT No.: PCT/JP2017/036202
§ 371 (c)(1),
(2) Date: Mar. 22, 2019

(87) PCT Pub. No.: WO2018/056472
PCT Pub. Date: Mar. 29, 2018

(65) Prior Publication Data
US 2019/0274947 A1    Sep. 12, 2019

(30) Foreign Application Priority Data
Sep. 23, 2016 (JP) .............. JP2016-185331

(51) Int. Cl.
A61K 8/898 (2006.01)
A61K 8/04 (2006.01)
A61Q 3/02 (2006.01)
C08F 290/06 (2006.01)

(52) U.S. Cl.
CPC .............. *A61K 8/898* (2013.01); *A61K 8/042* (2013.01); *A61Q 3/02* (2013.01); *C08F 290/068* (2013.01); *A61K 2800/54* (2013.01); *A61K 2800/594* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 3,645,835 A | 2/1972 | Hodgson | |
| 2002/0197218 A1 | 12/2002 | Bernard et al. | |
| 2015/0004112 A1 | 1/2015 | Ritter et al. | |
| 2016/0282516 A1* | 9/2016 | Imafuku | .............. C08F 290/068 |
| 2016/0289368 A1* | 10/2016 | Satake | ................. C08G 18/672 |

FOREIGN PATENT DOCUMENTS

| | | | | |
|---|---|---|---|---|
| CN | 104277226 A | 1/2015 | | |
| CN | 104602886 A | 5/2015 | | |
| EP | 1106653 A2 | 6/2001 | | |
| JP | 05-255043 | 10/1993 | | |
| JP | 08-092038 | 4/1996 | | |
| JP | H1149836 A | 2/1999 | | |
| JP | 2001146522 A | 5/2001 | | |
| JP | 2002322034 A | 11/2002 | | |
| JP | 2003342128 A | 12/2003 | | |
| JP | 2011105639 A | 6/2011 | | |
| JP | 2013043853 A | 3/2013 | | |
| KR | 101646004 B1 * | 8/2016 | ............. | A61K 8/898 |
| WO | 2007060710 A1 | 5/2007 | | |
| WO | 2014177627 A1 | 11/2014 | | |
| WO | WO-2015001811 A1 * | 1/2015 | ............ | C08F 218/04 |
| WO | 2016066610 A1 | 5/2016 | | |
| WO | 2016066613 A1 | 5/2016 | | |
| WO | 2018056472 A1 | 3/2018 | | |

OTHER PUBLICATIONS

Google English Translation of KR101646004 ([retrieved from on-line website: https://patents.google.com/patent/KR101646004B1/en]) (Year: 2016).*
International Search Report and Written Opinion for International Patent Application No. PCT/JP2017/036202, dated Dec. 26, 2017.
Supplementary European Search Report for European Application No. 17853239.6, dated Mar. 18, 2020.

* cited by examiner

*Primary Examiner* — Kyung S Chang
(74) *Attorney, Agent, or Firm* — Dorsey & Whitney LLP

(57) ABSTRACT

A nail cosmetic composition contains a silicone macromonomer as a base material having at least two polymerizable functional groups and a polymerization initiator with respect to the silicone macromonomer. A method of using a nail cosmetic composition includes a painting step of painting a nail cosmetic composition described above on a nail and a curing step of exposing the nail cosmetic composition to light with an illuminance of 80 mW/cm² or less at dominant wavelength at an exposure time within three minutes per one layer to cure the nail cosmetic composition. The nail cosmetic resin contains a silicone unit in which a silicone macromonomer has been polymerized as the base material having at least two polymerizable functional groups.

18 Claims, No Drawings

COSMETIC COMPOSITION FOR NAILS, METHOD OF USING SAME, AND COSMETIC RESIN FOR NAILS

RELATED APPLICATION

The present application claims priority to Japanese Patent Application Number 2016-185331 filed on 23 Sep. 2016, titled "Nail Cosmetic Composition, Method of Using Same, and Nail Cosmetic Resin," assigned to Menicon Co., Ltd.

TECHNICAL FIELD

The present disclosure relates to a cosmetic composition for fingernails, a method of using same, and cosmetic resin for fingernails.

BACKGROUND ART

Conventionally, nail cosmetic resins are divided into nail polishes used in manicuring, where nitrocellulose and/or acrylic resin are the main component of the resin, and gel nails. Nail polishes typically include nitrocellulose and/or acrylic resin. These cosmetic resins, when used in nail polishes are dissolved in an organic solvent such as toluene, butyl acetate, ethyl acetate, or the like. The resulting solution may then receive a colorant, and the resulting solution may then be painted onto a nail and allowed to dry. Nail polish has a distinctly irritating odor, due to the presence of solvent in the final polish. Additionally, while inexpensive, the durability of traditional nail polish is somewhat limited; typically the dried nail polish only lasts from about 3 days to one week before pieces are chipped and flake off. Additionally, to fully remove traditional nail polish, harsh chemicals, such as acetone, are typically used.

In contrast, gel nails are formed of photocurable materials, such as a monomer mixture. Typically, gel nails include a mixture of an initiator and a polymerizable component such as a urethane oligomer, acrylic monomer, or the like. This mixture may be painted on a nail and subsequently cured by means of UV curing with a cold-cathode fluorescent lamp (CCFL) or a light emitting diode (LED). Of the two types of nail cosmetic resins, gel nails have attracted attention in recent years because of their excellent finish glossiness, adherence to nails, durability, reduced odor emission, and comparatively short drying or curing time. Gel nail resin is typically applied with 2-hydroxyethyl methacrylate and a crosslinking agent in addition to a urethane oligomer, hydrophobic monomer, or the like. This gel nail composition may then be cured in the presence of a photo-initiator, thereby obtaining a rigid resin of high durability. In most instances, the cured gel nail exhibits high durability, often lasting 3 weeks or more before there is any structural degradation. This durability provides a desired strength that is sought after by many specialists, such as guitarists and baseball players. Gel nails are often applied to a user's nail in layers, which may include a base layer on the user's nail, a color layer (which may include art or a picture), and a finishing top gel Due to their durability, traditional gel nails were typically removed at the salon via a sanding procedure.

Fingernails and toenails are composed of a keratin nail plate with thin plate shaped keratinocytes adhered closely thereto. The base of the nail and the nail bed are the portions of the nail that have insufficient formation of a nail plate and are not sufficiently keratinized. Nails continuously grow and change, and the cells under the nail plate cause the evaporation of moisture through the nail plate. In order to allow for this natural evaporation it is considered necessary for a gel nail resin to be permeable to oxygen and water vapor. Additionally, the failure of traditional gel nail resins to be permeable to oxygen and water vapor can result in an environment that facilitates the growth of bacteria such as *pseudomonas* on and under the nail, resulting in nail discoloration.

Prior art nail polish resin compositions may contain a silicone component in an attempt to achieve oxygen permeability, or the ability of the material to allow oxygen to pass to the nail surface. However, prior art nail polishes are presumed to exhibit low oxygen permeability and negligible water permeability and may have other properties which make them undesirable for use as a gel nail resin. For example, Japanese Unexamined Patent Application Publication No. 2003-342128 describes a composition that includes a high molecular weight linear siloxane polymer. Mixture of this polymer with a gel nail composition to obtain a gel nail composition having high oxygen permeability will result in dissolution failure and phase separation. Consequently, a uniform composition is difficult to obtain. Even if a uniform dissolution state can be obtained as a gel nail composition, this composition becomes cloudy when applied to a nail and allowed to cure, or phase separation occurs, creating a surface that becomes brittle and dull.

SUMMARY OF INVENTION

According to one exemplary embodiment, a gel nail cosmetic composition is configured to be applied to the surface of a nail and to form a nail cosmetic resin on a nail, wherein the gel nail cosmetic composition, when cured to form a resin has a moisture transpirability of greater than about 15 g/m²·hr.

According to one exemplary embodiment, the gel nail cosmetic composition to be applied to the surface of a nail and to form a nail cosmetic resin on a nail, wherein the gel nail cosmetic composition form resin has a moisture transpirability is greater than about 28 g/m²·hr.

According to one exemplary embodiment, the gel nail cosmetic composition to be applied to the surface of a nail and to form a cured nail cosmetic resin on a nail, wherein the gel nail cosmetic composition form resin has an oxygen permeability coefficient of the nail cosmetic resin is 25 barrer or greater.

According to another exemplary embodiment, the gel nail cosmetic composition includes a base material including a silicone macromonomer having at least two polymerizable functional groups, and a polymerization initiator configured to selectively initiate polymerization of the silicone macromonomer.

According to one exemplary embodiment, the silicone macromonomer of the the gel nail cosmetic composition has a structure according to the chemical formula:

wherein R is a polymerizable functional group, A is a connecting atom or group, B is a silicone containing group, and X is any whole number.

According to one exemplaty embodiment, the silicone macromonomer includes at least a polysiloxane structure as the silicone containing group and a urethane bond and an ether bond as the connecting group.

According to yet another exemplary embodiment, the silicone macromonomer includes a first silicone macromonomer having a first structure and a second silicone macromonomer having a second structure, wherein a chain length of the second structure is longer than a chain length of the first structure, and wherein the second silicone macromonomer is included in a weight ratio greater than or equal to that of the first silicone macromonomer.

According to yet another exemplary embodiment, the silicone macromonomer has a structure according to the chemical formula:

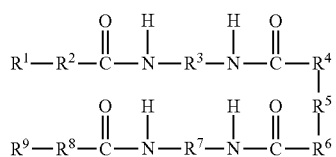

(2)

wherein $R^1$ and $R^9$ are terminal polymerizable functional groups; $R^2$, $R^4$, $R^6$, and $R^8$ are groups having a structure of an alkoxy group; $R^3$ and $R^7$ are each a cyclic group; and $R^5$ is a polysiloxane group.

According to yet another exemplary embodiment, the silicone macromonomer of the gel nail cosmetic composition has a structure according to the chemical formula:

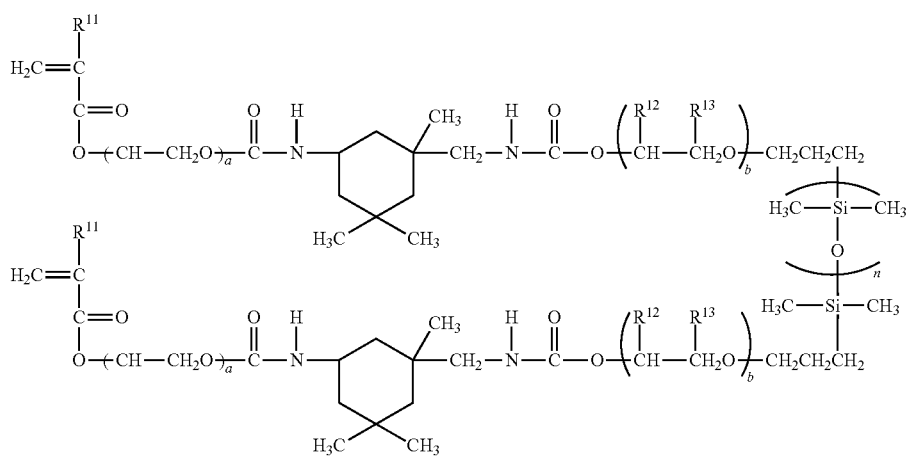

(3)

wherein $R^{11}$, $R^{12}$, and $R^{13}$ are each a hydrogen or an alkyl group having 3 or fewer carbon atoms, and wherein a and b are each between 1 and 15.

According to yet another exemplary embodiment the silicone macromonomer includes at least two chemically distinct silicone macromonomers.

According to yet another exemplary embodiment, the gel nail cosmetic composition includes a first silicone macromonomer wherein a=b=1, and a second silicone macromonomer wherein a≥1 and b>1, wherein a mass ratio of the first silicone macromonomer with respect to the second silicone macromonomer is from about 10/90 or more to about 50/50 or less.

According to yet another exemplary embodiment the silicone macromonomer includes from about 2 weight percent to about 80 weight percent of the base material.

According to yet another exemplary embodiment the polymerization initiator of the gel nail cosmetic composition includes from about 2 weight percent to about 15 weight percent of the base material.

According to yet another exemplary embodiment, the base material further includes at least one of acryloyl morpholine, N,N-diethylacrylamide, and 2-methoxyethyl acrylate.

According to yet another exemplary embodiment the gel nail cosmetic composition includes a crosslinking agent, wherein the crosslinking agent includes at least one of a bifunctional crosslinking agent, a trifunctional crosslinking agent, or a tetrafunctional crosslinking agent.

According to yet another exemplary embodiment the gel nail cosmetic composition has a viscosity of from about 50 mPa·s to about 38,000 mPa·s as measured at 20° C. using a rotational viscometer.

According to yet another exemplary embodiment, the cured nail cosmetic composition exhibits a surface gloss of 5 or more at 20° or 25 or more at 60° as measured by a gloss meter.

An exemplary method of using a nail cosmetic composition to form a cured nail cosmetic composition on a nail includes painting a nail cosmetic composition on a nail, and exposing the nail cosmetic composition to light with an illuminance of 80 mW/cm² or less at dominant wavelength for less than about three minutes to cure the nail cosmetic composition, wherein the cured nail cosmetic composition exhibits a moisture transpirability of greater than about 25 g/m²·hr.

According to yet another exemplary embodiment the method of using a nail cosmetic composition to form a cured nail cosmetic composition on a nail includes, wherein the cured nail cosmetic composition has an oxygen permeability greater than about 25 barrer.

According to yet another exemplary embodiment the cured nail cosmetic composition has an oxygen permeability greater than about 50 barrer.

According to yet another exemplary embodiment the cured nail cosmetic composition has an oxygen permeability greater than about 75 barrer.

According to yet another exemplary embodiment the cured nail cosmetic composition has an oxygen permeability greater than about 100 barrer.

According to yet another exemplary embodiment the nail cosmetic composition comprises a base material including: a silicone macromonomer having at least two polymerizable functional groups, and a polymerization initiator configured to selectively initiate polymerization of the silicone macromonomer.

DESCRIPTION OF EMBODIMENTS

The principles described herein include a nail cosmetic composition and a nail resin having excellent oxygen permeability and water transpirability, as well as methods of using the same. The nail cosmetic composition also exhibits high glossiness, homogeneity, hardness, and durability. As used herein, the phrase "transpirability" is meant to be understood as an ability to pass off or give passage to vapor or gas through a surface. The nail cosmetic compositions described herein may also having excellent coatability characteristics and may provide a pleasing appearance when applied to the surface of a nail. The nail cosmetic compositions and nail resins described herein may include a silicone containing macromonomer. In some cases, the silicone macromonomer may be polymerized as a base material for the nail cosmetic composition. In some cases, the silicone macromonomer may include at least two polymerizable functional groups and may be a base material for the nail cosmetic composition. In some cases, the nail cosmetic composition may also include a polymerization initiator for the silicone macromonomer.

In some embodiments, a method of using a nail cosmetic composition as described herein may include painting a nail cosmetic composition, such as a resin as described herein, on a nail, and a curing step. The curing step may include exposing the nail cosmetic composition to light with an illuminance of 80 mW/cm² or less at a dominant wavelength, for example of 365 nm or 405 nm. The exposure time may vary, but according to one embodiment, the curing step may occur at an exposure time of less than about three minutes per layer of nail cosmetic composition.

In some prior art nail cosmetic compositions including silicone, the silicone component may dissolve oxygen. This dissolved oxygen may result in an increased amount of unpolymerized components after curing, also referred to as polymerization inhibition. Polymerization inhibition may also suppress the degree of polymerization of the resin surface, thereby decreasing the surface luster, or glossiness, of the nail cosmetic composition and leading to surface stickiness. In some embodiments of the present disclosure, the silicone macromonomer of the nail cosmetic composition as described herein may provide a good glossy surface texture with excellent durability and hardness that does not have surface stickiness.

In some embodiments, a nail cosmetic composition may include a silicone macromonomer having at least two polymerizable functional groups as a base material and may also include a polymerization initiator with respect to the silicone macromonomer. In some cases, using a silicone macromonomer for at least one component of this nail cosmetic composition can further increase oxygen permeability and/or moisture transpirability of the nail cosmetic composition as compared to other gel nail cosmetic compositions. Further, in some cases, a nail cosmetic composition including silicone macromonomer having polymerizable functional groups as one component thereof may not only increases the oxygen permeability and moisture transpirability of the resin obtained after curing the composition, but may also improve the elasticity, flexibility, mechanical strength, and durability of the cured nail cosmetic composition. In some embodiments, for example, an acryloyl group, methacryloyl group, vinyl group, allyl group, or the like may be the polymerizable functional group. As used herein, an acrylate group having an acryloyl group and a methacrylate group having a methacryloyl group are collectively referred to as (meth)acrylate.

In some embodiments, the silicone macromonomer which may be included in the nail cosmetic composition is not limited. For example, in some cases, the silicone macromonomer may have the structure of Chemical Formula 1, provided below. In Chemical Formula 1, X may be any whole number, for example, 4 or less, or 2 or less. R represents a polymerizable functional group, or may be any of the functional groups described above. A represents a connecting unit, or may be those containing a carbon chain. B is a silicone unit containing Si. In some embodiments, the silicone macromonomer may have a polysiloxane structure as a silicone unit. For example, a polydimethylsiloxane structure, or the like, can be exemplified as this polysiloxane structure. The silicone macromonomer may have a urethane bond or an ether bond as the connecting unit in the molecule. In some cases, this structure may allow the resin to have excellent oxygen permeability moisture transpirability, elasticity, and durability as described herein. In some cases, for example, the silicone macromonomer may contain at least a polysiloxane structure, a urethane bond, and an ether bond.

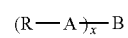

(where X is an arbitrary number, R is a polymerizable functional group, A is a connecting unit, and B is a silicone unit.)

In some embodiments, the silicone macromonomer may have the structure of Chemical Formula 2. In Chemical Formula 2, $R^1$ and $R^9$ may represent terminal polymerizable functional groups, for example either an acryloyl group or methacryloyl group, and may be the same or different. In some cases, $R^2$, $R^4$, $R^6$, and $R^8$ may represent a group having structure of an alkoxy group, wherein at least two of these may be the same or different. In some embodiments, the foregoing $R^2$, $R^4$, $R^6$, and $R^8$ may have a structure in which the structure of the alkoxy group is repeated a predetermined number of times. For example, any one of $R^2$, $R^4$, $R^6$, and $R^8$ may be an alkoxy group, such as a methoxy group, an ethoxy group, a propoxy group, and the like. In some cases, this alkoxy group may further have a substituent such as an alkyl group, or the like bonded thereto. In some embodiments, $R^3$ and $R^7$ may be groups having a cyclic structure and may be the same or different. In some cases, $R^3$ and $R^7$ may have a cyclohexane structure as the cyclic structure, or may have a plurality of substituent groups, such as one or more alkyl groups, or the like. In some embodiments, a methyl group, an ethyl group, a propyl group, or the like, can be exemplified as the alkyl group. In some embodiments, $R^5$ may represent a group having a polysiloxane structure. The polysiloxane structure is not limited; it may be a polydimethylsiloxane structure, for example.

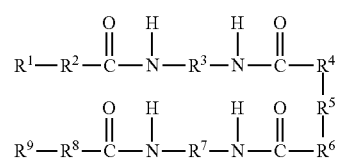

(where $R^1$ and $R^9$ represent either an acryloyl group or a methacryloyl group; $R^2$, $R^4$, $R^6$, and $R^8$ represent a group containing the structure of an alkoxy group, wherein at least two of either of the foregoing may be the same or different; $R^3$ and $R^7$ represent a group having a cyclic structure and may be the same or different; and $R^5$ represents a group having a polysiloxane structure.)

In some embodiments, the silicone macromonomer may have the structure of Chemical Formula 3. In Chemical Formula 3, $R^{11}$-$R^{13}$ may represent any of hydrogen and an alkyl group having 3 or less carbon atoms and may be the same or different. Furthermore, in Chemical Formula 3, a and b may represent a number from between 1 and 15, and may be the same or different. In some cases, n may express a repeating number of a polysiloxane structure, and may be a number from between about 10 to about 60. In some embodiments, this repeating number n may be from about 10 to about 40. In some cases, the silicone macromonomer may have the formula of Chemical Formula 3, wherein a=b=1. However, in some embodiments, a=1 and b=10. The silicone macromonomer of Chemical Formula 3 is explained in detail in Japanese Patent Application No. 5604154 and International Patent Publication No. WO 2015/092859, which are hereby incorporated by reference in their entireties.

to polymerization inhibition at the time of resin formation as compared to a nail cosmetic composition that does not include a silicone macromonomer.

In some embodiments, the silicone macromonomer may be used individually or mixed in combinations of two or more types. That is, in some embodiments, the nail cosmetic composition may contain a first silicone macromonomer having a first structure and a second silicone macromonomer having a second structure in which a portion thereof is different from the first structure. For example, in some cases the nail cosmetic composition may contain a first silicone macromonomer having a first structure and a second silicone macromonomer having a second structure, wherein the chain length of the second structure is longer than that of the first structure. In these cases, the second silicone macromonomer may be included at the same or more mass ratio than the first silicone macromonomer. For example, in some embodiments, two or more types of compounds having the structure of Chemical Formula 3 may be included as the silicone macromonomer. In some embodiments, by including silicone macromonomer compounds having two or more types of different structures from each other, it is possible to adjust the viscosity of the nail cosmetic composition, thereby improving coatability. In some embodiments, the resin obtained by combining compounds of two or more (3)

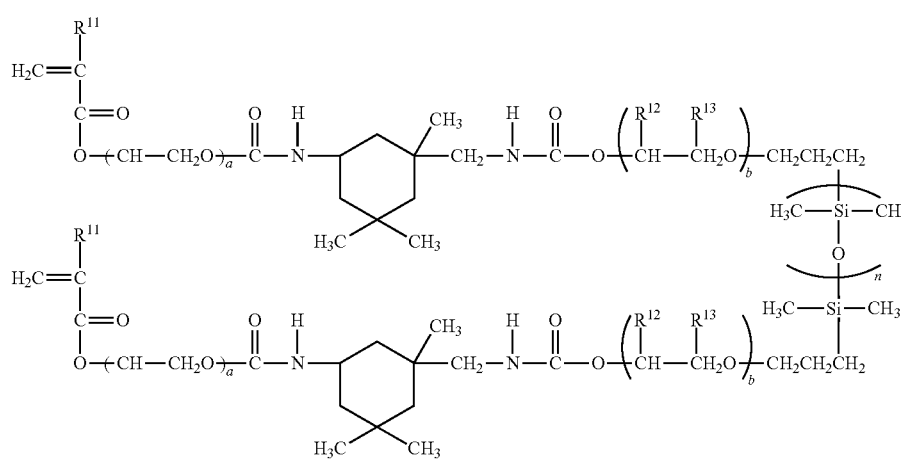

(where $R^{11}$-$R^{13}$ represent hydrogen or an alkyl group having 3 or fewer carbon atoms and each may be the same or different; n represents a number from 10 or more to 60 or less; a and b each represent a number from 1 or more to 15 or less, and may be the same or different.)

In some embodiments, the silicone macromonomer may be in the range of 2 parts by weight or more to 80 parts by weight or less; in the range of 10 parts by weight or more to 78 parts by weight or less; in the range of 20 parts by weight or more to 77 parts by weight or less; relative to 100 parts by weight of the entire component of the base material, excluding the polymerization initiator or colorant or pigment. In some embodiments, the content of 2 parts by weight or more may make it possible to obtain increasingly higher oxygen and/or moisture transpirability as compared to a nail cosmetic composition that does not include a silicone macromonomer. In some cases, the content of 80 parts by weight or less may make it possible to further suppress the decrease in brightness and brittleness of the resin itself and to further suppress the increase of the residual portion generated due types in such a manner may exhibit high oxygen and/or moisture transpirability and high glossiness, with a reduction in brittleness as compared to gel nail cosmetic compositions that do not include a silicone macromonomer. For example, a first silicone macromonomer having the formula of Chemical Formula 3, wherein a=b=1 and a second silicone macromonomer having the formula of Chemical Formula 3, wherein a≥1 and b>1 may be included as the silicone macromonomer. In some embodiments, the first silicone macromonomer may have the formula of Chemical Formula 3, wherein 1≤a≤4 and/or 1≤b≤4, and the second silicone macromonomer may have the formula of Chemical Formula 3, wherein 1≤a≤12 and/or 5≤b≤12, or 1≤a≤10 and/or 8≤b≤10. Furthermore, in some embodiments, where the first and second silicone macromonomer have the formula of Chemical Formula 3, the ratio of repeating number (n1/n2), wherein n1 is the repeating number of first silicone macromonomer and n2 is the second silicone macromonomer, may be about ⅓ (20/60), about ½ (20/40), or about 1/1 (40/40). In some cases, for example, the weight ratio A/B of the first silicone macromonomer A with respect to the second silicone macromonomer B may be 10/90 or more, 15/85 or more, 20/80, or 25/75. This weight ratio A/B may be 50/50 or less, or 45/55 or less. In some embodiments, where the nail cosmetic composition comprises two types of silicone macromonomers in such ratios as described herein, the nail cosmetic composition may have such characteristics as excellent oxygen and/or moisture transpirability, glossiness, strength, and flexibility. In some embodiments where the silicone macromonomer has the formula of Chemical Formula 3, repeating numbers a, b, and n may be single digit numbers; however, the above-described silicone macromonomer may be a high molecular weight compound, so that mixing silicone macromonomers having several repeating numbers is common. In these cases, the repeating numbers a, b, and n of the silicone macromonomer may be an average value.

In some embodiments the nail cosmetic composition may contain a base component other than a silicone macromonomer. As such a base component, a monomer that has a polar group with excellent miscibility with a polymerization initiator or a silicone macromonomer may be adopted. In some embodiments, this monomer can impart glossiness, hardness, and durability to the resin obtained, and can provide a resin with less moisture absorption. In some embodiments, such a monomer may be, for example, a (meth)acrylate compound or a (meth)acrylamide compound including acryloyl morpholine, N,N-diethylacrylamide, and 2-methoxyethyl acrylate, which are copolymerization monomers. In some embodiments, these copolymerization monomers can be used individually or in combinations of two or more.

In some embodiments the nail cosmetic composition may further contain a crosslinking agent as a base material. Adding a crosslinking agent may impart increased hardness and glossiness to the resin after curing. Furthermore, in some embodiments where a crosslinking agent is the base material, the crosslinking agent may reduce the water content and water absorption of the resin and may increase the durability of the resin itself. Examples of a crosslinking agents include bifunctional crosslinking agents such as allyl (meth)acrylate, vinyl (meth)acrylate, (meth)acryloyloxyethyl (meth)acrylate, ethylene glycol di(meth)acrylate, diethylene glycol di(meth)acrylate, and the like; trifunctional crosslinking agents such as triallyl isocyanurate, trimethylolpropane triacrylate, glycerin triacrylate, and the like; tetrafunctional crosslinking agents such as pentaerythritol tetraacrylate, and the like; wherein these crosslinking agents can be used individually or in combinations of two or more. In some embodiments, the crosslinking agent or agents may be ethylene glycol di(meth)acrylate, triallyl isocyanurate, or pentaerythritol tetraacrylate. The use of a crosslinking agent in the nail cosmetic composition may allow for the ability to adjust the viscosity of the nail cosmetic composition and, moreover, the appearance of the resin can be made uniformly transparent, hard, and may have excellent surface gloss.

In some embodiments, the polymerization initiator contained in the nail cosmetic composition may include a radical photopolymerization initiator and/or a cationic polymerization initiator. In some embodiments, examples of the polymerization initiator may include acylphosphine oxide-based photopolymerization initiators such as 2,4,6-trimethylbenzoyl-diphenylphosphine oxide (TPO), bis(2,4,6-trimethylbenzoyl)phenylphosphine oxide, and the like. In some cases, examples of the polymerization initiator may include benzoin-based photopolymerization initiators such as methyl orthobenzoyl benzoate, benzoin methyl ether, benzoin ethyl ether, benzoin isopropyl ether, benzoin isobutyl ether, benzoin n-butyl ether, and the like. In some embodiments, examples of the polymerization initiator may include alkylphenone-based photopolymerization initiators such as 2-hydroxy-2-methyl-1-phenylpropane-1-one (HMPPO), 2,2-dimethoxy-1,2-diphenylethane-1-one (Irgacure 651), 1-[4-(2-hydroxyethoxy)-phenyl]-2-hydroxymethyl-1-propan-1-one (Irgacure 2959), 1-hydroxycyclohexyl phenyl ketone (Irgacure 184), and the like. In some embodiments, examples of the polymerization initiator may include thioxanthone-based photopolymerization initiators such as 1-phenyl-1,2-propanedione-2-(o-ethoxycarbonyl) oxime, 2-chlorothioxanthone, 2-methylthioxanthone, and the like. In some embodiments, these photopolymerization initiators may be used individually or in combinations of two or more types. In addition, in some cases, a photosensitizer may also be used together with a photopolymerization initiator. In some embodiments, the polymerization initiator may be included in the nail cosmetic composition in the range of 1.5 parts by weight or more to 20 parts by weight or less, in the range of 2 parts by weight or more to 15 parts by weight or less, in the range of 2 parts by weight or more to 10 parts by weight or less, with respect to 100 parts by weight of the base material.

In some embodiments, a colorant such as a dye, pigment, or the like may further be added to the nail cosmetic composition. However, applying only a colorant to a nail cosmetic composition may result in poor miscibility, so that it is difficult to obtain a uniform nail cosmetic composition. Therefore, in some embodiments a coloring composition, where the colorant to be used is coated with a binder such as a silicone resin, or the like may be included in the nail cosmetic composition. The colorant may be any suitable material known in the art or discovered in the future. In some embodiments the colorant may be contained in the nail cosmetic composition in the range of 3 parts by weight or more to 30 parts by weight or less; or in the range of 5 parts by weight or more to 20 parts by weight or less relative to 100 parts by weight of the base material.

In some embodiments, the nail cosmetic composition may also be substantially free of an organic solvent. As used herein, "substantially free of" may refer to an organic solvent contained as an impurity of a polymerizable component and may be found in the nail cosmetic composition in an amount less than approximately 1% mass as a composition ingredient. In some embodiments, the organic solvent is an organic compound added to adjust the viscosity of the nail cosmetic composition and may not have a polymerizable reactive group. Examples of organic solvents may include alcohol, acetone, methyl ethyl ketone, dimethylformamide, dimethylsulfoxide, acetonitrile, N-methyl-2-pyrrolidone, dimethoxyethane, and the like.

In some embodiments the nail cosmetic composition may have a relatively moderate viscosity. In some embodiments, the viscosity of the nail cosmetic composition may be in the range of 50 (mPa·s) or more to 38,000 (mPa·s) or lower as measured at 20° C. by a rotational viscometer, in the range of 50 (mPa·s) or more to 30,000 (mPa·s) or lower, or in the range of 50 (mPa·s) or more to 26,000 (mPa·s) or lower. In some embodiments, where the viscosity of the nail cosmetic composition is 38,000 (mPa·s) or lower, or 30,000 (mPa·s) or lower, the viscosity may suppress the generation of bubbles or unevenness at the time of application of the composition to a nail. In some embodiments where the viscosity may be 50 (mPa·s) or higher, the viscosity can suppress the occurrence of liquid dripping, making it possible to form a coating film of a substantial and desirable thickness on a nail.

In some embodiments a method of using a nail cosmetic composition includes a painting step of painting a nail cosmetic composition as described herein on a nail, and a curing step. In some embodiments the curing step may include exposing the nail cosmetic composition to light with an illuminance of 80 mW/cm$^2$ or less at a dominant wavelength with an exposure time of less than about three minutes per one layer in order to cure the nail cosmetic composition.

In some embodiments, the painting step may include painting a nail cosmetic composition on a nail using a brush or painting brush, for example. In some embodiments, a nail cosmetic composition may also be painted on a nail in more than one layer, for example, as a base layer, a decorative layer, and a protective layer. In some cases of painting two or more layers of the nail cosmetic composition, the nail cosmetic composition may be cured after each layer has been applied. Thus, in some embodiments a method of using a nail cosmetic composition may include a plurality of repeated painting and curing steps. In some embodiments, the thickness of the layer may be appropriately set depending on the viscosity of the composition; for example, it may be set in the range of 100 μm or more to 1000 μm or less.

In some embodiments, the curing step may use those polymerization lamps generally commercially available for use in curing gel nails. In some embodiments the light used to illuminate the nail cosmetic composition in the curing step may have the wavelength with the strongest illuminance among the emission spectra as the desired wavelength of the initiator included in the nail cosmetic composition. In some embodiments a UV lamp or an LED lamp having a main wavelength of 365 nm or 405 nm may be used in the curing step. In some embodiments, in view of the effects of the UV light and heat from the lamp to the exposed nails and the effect of polymerization heat accompanying the curing process, the illuminance at the dominant wavelength may be about 80 mW/cm$^2$ or less, about 40 mW/cm$^2$ or less, about 15 mW/cm$^2$ or less, or about 10 mW/cm$^2$ or less. In some embodiments, in view of the time spent in beauty salons or in the home, the irradiation time may be set to less than about three minutes, or less than two minutes for curing one layer of nail cosmetic composition on the nail.

In some embodiments, the nail cosmetic resin to be applied to the surface of a nail contains a silicone unit polymerized by a silicone macromonomer as a base material having at least two polymerizable functional groups as described herein. In some embodiments the nail cosmetic resin may be a gel nail, for example, and the nail cosmetic composition as herein may be cured by the use method described above to form the nail cosmetic resin. In some embodiments, after curing, the nail cosmetic resin may have the characteristics of an even and uniform appearance, sufficient gloss, excellent hardness and non-brittleness, and a durability that allows for the resin to be worn for several weeks.

Considering the negative effects on cells at the portion of the nail with insufficient keratinization at the nail bed, and the moisture evaporation through the nail from the cells under the nail, in some embodiments the nail cosmetic resin may have excellent oxygen permeability and moisture transpirability. In some embodiments, the oxygen permeability of the nail cosmetic resin is 25 barrer or more, 30 barrer or more, 50 barrer or more, 100 barrer or more, 150 barrer or more, 200 barrer or more, or 250 barrer or more.

The moisture transpirability, also referred to as the moisture vapor permeability, of the nail cosmetic resin refers to the ability of moisture or water vapor to pass through the nail cosmetic resin, for example due to biological processes which may occur in the nail bed. A high moisture transpirability is desirable because it allows for the natural evaporative removal of moisture from the nail and nail bed, which can maintain nail health and prevent problems commonly associated with gel nails. Moisture transpirability is also desirable for devout Muslim adherents. Unless a nail cosmetic composition is porous, Muslim adherents cannot wear it because it interferes with wudu or ablution—the Islamic procedure of washing parts of the body before prayer—wherein water has to touch every part of the adherent's body. The moisture transpirability is measured in the amount of water (g) which pass through the surface of the nail cosmetic resin (m$^2$) per unit of time (hr.). In some embodiments, the moisture transpirability of the nail cosmetic resin may be unexpectedly high, in some cases higher even than the moisture transpirability of typical nail polishes. In some embodiments, the nail cosmetic resin may have a moisture transpirability of greater than 15 g/m$^2$·hr, greater than 20 g/m$^2$·hr, greater than 25 g/m$^2$·hr, greater than 26 g/m$^2$·hr, greater than 27 g/m$^2$·hr, greater than 28 g/m$^2$·hr, greater than 29 g/m$^2$·hr, greater than 30 g/m$^2$·hr, or greater. In some embodiments, the moisture transpirability may be greater than 35 g/m$^2$·hr. or more. Thus, in some embodiments, the nail cosmetic compositions and nail cosmetic resins formed therefrom as described herein may provide the beneficial hardness, durability, and aesthetic characteristics that are typical of gel nails, while providing unexpectedly high oxygen permeability and moisture transpirability. As described herein, these high oxygen permeability and moisture transpirability values may allow for a healthy nail and nail bed while the nail cosmetic resin is applied to the nail, and may inhibit or suppress the formation of green nail syndrome (*Pseudomonas* nail infection).

In some cases, a certain degree of moisture in the nail cosmetic resin is desirable in view of safeguarding the health of the cells of the nail; however, too high a moisture content in the nail cosmetic resin may increase the flexibility of the resin itself, for example, the resin may unintentionally peel off immediately after application or have poor durability during work with water. Accordingly, in some embodiments, the moisture content of the cured nail cosmetic resin may be in the range of 3 wt % or more to 20 wt % or less; or in the range of 3 wt % or more to 18 wt % or less.

In some cases it is desirable for the nail cosmetic resin to have a high hardness low-molecular residue in the resin in order to safeguard the health of the cells of the nail. In some embodiments, the extraction rate (residue rate) (wt %), which is the quantity of the ingredient dissolved after the cured resin is immersed overnight in an organic solvent (acetone), is a relatively small value. Generally, after curing, the unpolymerized component remaining on the surface of the nail cosmetic resin may be wiped off and removed with an organic solvent or an aqueous solution of organic solvent; however, for those nail cosmetic resins with a high extraction rate the amount of unpolymerized component removed by wiping is significant. Therefore, the approximate hardness of the entire nail cosmetic resin may be estimated by evaluating the amount of extraction of the nail cosmetic resin, with a higher extraction rate indicating a lower hardness value. In some embodiments, the nail cosmetic resin described herein may have a substantially higher hardness than other similar nail cosmetic resins that do not include a silicone macromonomer.

Since nail cosmetic resins are typically used for aesthetic purposes, in some embodiments the nail cosmetic resin described herein may excellent optical properties and high surface glossiness as can be measured with a gloss meter. After curing, any unpolymerized component may be wiped off and removed with an organic solvent or an aqueous solution of an organic solvent, and the surface glossiness as measured by a gloss meter may be 5 or more at a measurement angle of 20°, and 25 or more at 60° with respect to the resin. In some embodiments the surface glossiness may be close to about 100.

EXAMPLES

Specific examples of how to prepare the nail cosmetic composition and the nail cosmetic resin of the present disclosure are described herein below as experimental examples. Such examples are intended to aid in the understanding of the present disclosure and are not intended to limit the scope of the present disclosure in any way. Experimental Examples 1-20 and 23-39 are working examples and Experimental Examples 21, 22, and 40-45 are comparative examples. This present disclosure is not limited to the following working examples, and it shall be readily understood that various embodiments can be implemented as long as they belong within the technical scope of this disclosure.

The silicone macromonomers of the examples described herein may have the structure of one or more of Chemical Formula 4, 5, or 6, provided below. In these cases, n is a number from 10 or more to 60 or less.

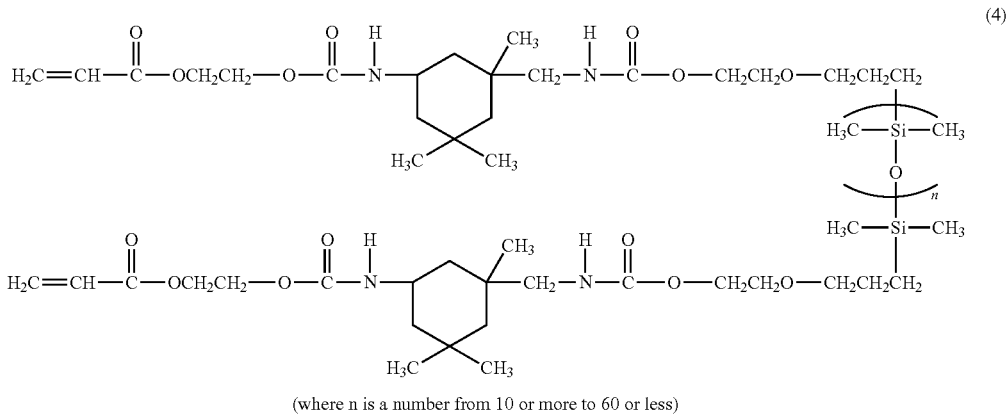

(4)

(where n is a number from 10 or more to 60 or less)

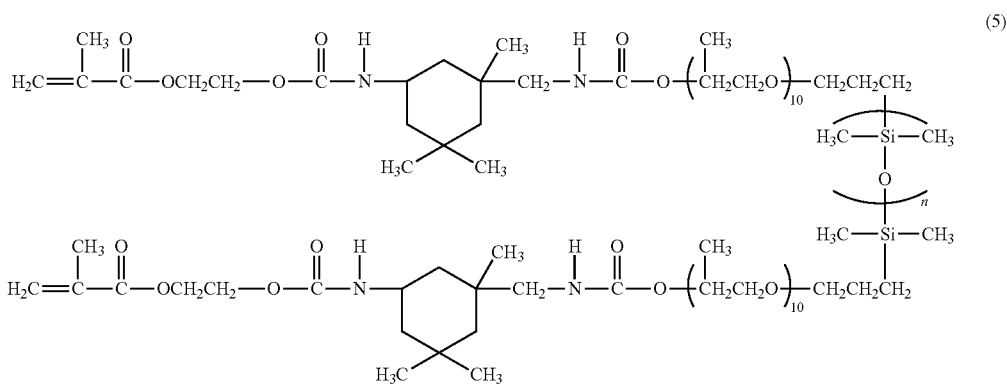

(5)

(where n is a number from 10 or more to 60 or less)

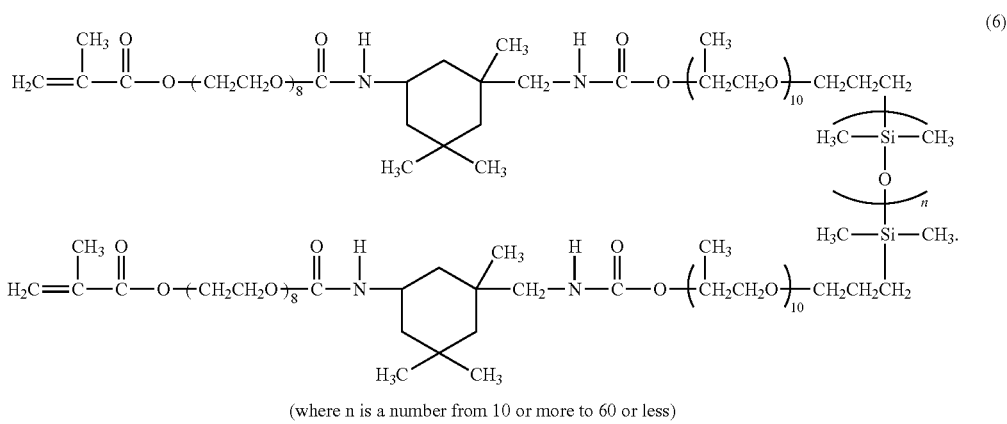

(6)

(where n is a number from 10 or more to 60 or less)

The abbreviations of the compounds used in the Experimental Examples are shown below. The macromonomer is a high molecular weight compound, and the repeating numbers a, b, and n represent average values.

Base Material
Silicone macromonomer
SiDA-A: A silicone macromonomer with n of Chemical Formula 4 about 60
SiDA-B: A silicone macromonomer with n of Chemical Formula 4 about 40
SiDA-C: A silicone macromonomer with n of Chemical Formula 4 about 20
SiDA-D: A silicone macromonomer with n of Chemical Formula 4 about 10
SiDA-E: A silicone macromonomer with n of Chemical Formula 5 about 40
SiDA-F: A silicone macromonomer with n of Chemical Formula 6 about 60
Copolymerization monomer
ACMO: Acryloyl morpholine
DEAA: N,N-diethylacrylamide
2-MTA: 2-methoxyethyl acrylate
Crosslinking agents
EDMA: Ethylene glycol dimethacrylate
TAIC: Triallyl isocyanurate
PETA: Pentaerythritol tetraacrylate
Polymerization Initiators
TPO: Diphenyl(2,4,6-trimethylbenzoyl)phosphine oxide
IRG 651 (Irgacure 651: 2,2-Dimethoxy-2-phenylacetophenone
TRIS: Tris(trimethylsiloxy)silylpropyl methacrylate
SiST: Tris(trimethylsiloxy)silylstyrene The compounding ratios shown in Tables 1-4 below were used, wherein each component was weighed in a brown glass vial bottle having a capacity in the range of 10-50 mL and mixed well to prepare nail cosmetic compositions of Experimental Examples 1-20 and as described herein. For the purpose of uniformly dissolving the polymerization initiator, which is a solid component, during mixing, the preparation was carried out by mixing all components except the silicone macromonomer and then subsequently mixing the silicone macromonomer. No organic solvent was added. Calgel, a commercially available product of MOGA BROOK Co., Ltd., was used as the initiator in Experimental Example 21, and Para gel, a commercially available product of Nail Select Co., Ltd., was used as the initiator in Experimental Example 22.

The compounding ratios shown in Tables 5-6, provided below, were used, where each component was weighed in a brown glass vial bottle having a capacity in the range of 10-50 mL and mixed well to prepare nail cosmetic compositions of Experimental Examples 23-39. For the purpose of uniformly dissolving the polymerization initiator, which is a solid component, during mixing, the preparation was carried out by a procedure of mixing all components except the silicone macromonomer and subsequently mixing the silicone macromonomer. No organic solvent was added. As shown in Table 7, provided below, for comparison with the compounding ratio using the components of Experimental Examples 21 and 22 as the main components, each component was weighed in a brown glass vial bottle having a capacity in the range of 10-50 mL and mixed well to prepare nail cosmetic compositions of Experimental Examples 40-45.

Procedure

The nail cosmetic composition was allowed to cure after mixing to evaluate its characteristics. The nail cosmetic composition was painted using a commercially available brush for gel nails on a plate made of polypropylene (PP) or a nail tip made by acrylonitrile-butadiene-styrene (ABS), and light was subsequently irradiated to cure it. In Experimental Examples 1-11, irradiation was performed for two minutes using a commercially available nail curing unit from DOUYU, Ltd., equipped with four 9 W-UV lamps (365 nm) to obtain a gel nail cosmetic resin. The illuminance of this lighting unit as measured with a UIT-101, UVD-365PD luminometer, commercially available from Ushio, Inc. and was found to be about 1.9 mW/cm$^2$. In Experimental Examples 12-14, a CCFL-LED lamp (36 W, N-218) commercially available from DOUYU, Ltd., Nail Garden was used for curing. In this lighting unit, the illuminance at a wavelength of 365 nm was about 1.9 mW/cm$^2$ and the illuminance at a wavelength of 405 nm was about 8 mW/cm$^2$ directly underneath a UIT-150 CCFL lamp and 27 mW/cm$^2$ directly underneath a UVD-S405 LED lamp, both commercially available products from Ushio, Inc. The standard curing time of the devices was set to 60 seconds. In Experimental Examples 15-20, curing was carried out using a commercially available LED lamp manufactured by Sweets Co., Ltd. (12V-6 W, 6 UVT, S/N 0008767). In this lighting unit, the illuminance at a wavelength of 365 nm was about 0.7 mW/cm$^2$ and the illuminance at a wavelength of 405 nm was about 31 mW/cm$^2$ directly underneath the LED lamp. The standard curing time of the devices was set to 30 seconds. In Experimental Examples 23-45, irradiation with a nail curing unit (Paragel LED Paralite IV) equipped with an 18 W-LED lamp (405 nm) for 1 minute gave a nail cosmetic resin. In this irradiation unit, the illuminance measured at 365 nm is about 0.1 mW/cm$^2$ (luminometer UIT-101, UVD-365 PD manufactured by Ushio Inc.), the illuminance at a wavelength of 405 nm is about 12 mW/cm$^2$ (luminometer UIT-150, UVD-S 405 manufactured by Ushio Inc.).

After irradiation, the unpolymerized components remaining on the surface were removed with an absorbing paper (a tissue paper) that had been impregnated with 50% aqueous solution of 2-propanol.

Coatability

The coatability to the nail tip as the characteristic of the nail cosmetic composition was confirmed and evaluated based on the following evaluation criteria. Those samples having favorable viscosity, excellent coatability, and an easily formed and uniform coating film were rated "AA". Those samples having favorable viscosity, good coatability, and a uniform coating film were rated "A". Those samples having slightly high fluidity, relatively good coatability, and a uniform coating film formed were rated "B". Those samples having high viscosity, producing bubbles or lumps, or low viscosity causing prominent dripping were rated "C".

Viscosity

An E-type rotational viscometer (TVE-20H) manufactured by Toki Sangyo, Co., Ltd. was used to measure the viscosity at 20° C.

Appearance After Curing

The appearance in terms of transparency, cloudiness, and unevenness after light irradiation was performed and the unpolymerized components were removed was evaluated based on the following evaluation criteria. Those samples that were transparent, without cloudiness, and with a uniform appearance without unevenness were rated "A". Those samples with slight unevenness and with dullness and turbidity were rated "B". Those samples with uneven appearance or no transparency and with white turbidity were rated "C".

Gloss/Visual Inspection

The nail cosmetic resin obtained was confirmed by visual inspection, and its glossiness was evaluated based on the following evaluation criteria. Those samples with excellent gloss on the entire resin were rated "AA"; those samples with good gloss on the entire resin, "A"; those samples with unevenness and no gloss in some part of the resin, "B"; and those samples exhibiting a dull appearance without gloss to the entire resin, "C".

Hardness and Brittleness

The properties of the nail cosmetic resin were confirmed by visual inspection, and the hardness and brittleness were evaluated based on the following evaluation criteria. Those samples with extremely high hardness and without cracks or chips even after pressure was applied were rated "AA", those with high hardness and without cracks or chips even after pressure was applied were rated "A", those with good hardness but cracks or chips occurred in some portion of the resin after pressure was applied after curing were rated "B", and those with weak hardness or resin easily cracked or chipped "C".

Durability

After the composition was painted on a nail and cured, the appearance after two weeks had passed was confirmed, and the durability was evaluated based of the following evaluation criteria. Those samples maintaining appearance and complete coating at least for two weeks were rated "A"; those having the resin peeling or separating from some part of the cuticle part and at the tip of the nail after two weeks, "B"; and those having the resin cracked or chipped on some part of the cuticle part and at the tip of the nail after two weeks, "C".

Extraction Rate

An extraction rate value was obtained by the equation $(W_1-W_2)/W1 \times 100(\%)$, where $W_1$ represents the weight of four sheets of resin that had been wiped with 2-propanol after the nail cosmetic composition was irradiated with light to cure it, and $W_2$ represents the weight of resin that had been immersed overnight (about 16 hours) in 30 mL of acetone at room temperature, taken out, subsequently dried for about three hours in a dryer at 105° C., and then cooled in a desiccator for about 30 minutes.

Moisture Content

The moisture content value was obtained by the equation $(W_3-W_4)/W_3 \times 100(\%)$, where $W_3$ represents the weight of four sheets of resin that had been wiped with 2-propanol after the nail cosmetic composition was irradiated with light to cure it, and $W_4$ represents the weight of resin that had been immersed in 30 mL of distilled water, allowed to stand as is overnight (about 16 hours) in a constant temperature water tank set at 20° C., taken out, and subsequently dried for about three hours in a dryer at 105° C., and cooled for about 30 minutes in a desiccator.

Oxygen Permeability Coefficient

The nail cosmetic composition was cured in a system closed by a mold for conveniently fabricating a PP plate in order to prepare a nail plate with a thickness of about 0.3 mm for use in the evaluation. No wiping with 2-propanol was carried out. Measurement was carried out using a GTG (GAS to GAS) analyzer manufactured by Rehder Development Company. The measurement time was two minutes at a temperature of 35° C., and the measured value obtained was converted to obtain a Dk value. The Dk value refers to the value of the oxygen permeability coefficient [$(cm^2/sec)-(mL-O_2/(mL-mmHg))$], and is obtained by multiplying the oxygen permeability coefficient value by $10^{11}$.

Gloss

After curing the nail cosmetic composition by irradiating light, two sheets of resin were wiped with an aqueous 2-propanol solution(505). Gloss meters corresponding to ISO 2813, ISO 7668, ASTM D 523, ASTM D 2457, DIN 67 530, JIS Z 8741, GM-268 Plus manufactured by Konica Minolta were then used to measure gloss at 20° and 60°, to determine a measurement value.

Results and Discussion

The results obtained after evaluating the compounding ratio (wt %) of the raw material, coatability, and the appearance after curing of the compositions in Experimental Examples 1-11 are summarized in Tables 1 and 2, below. The results obtained after evaluating the compounding ratio (wt %) of the raw material, coatability, the appearance after curing, gloss, hardness and brittleness, durability, extraction rate, water content, and oxygen permeability coefficient are summarized in Tables 3 and 4, below. The nail cosmetic compositions described in Experimental Examples 1-20 have excellent coatability and curability, as can be seen in Tables 1-4. It can be inferred that the silicone macromonomer is preferably contained in the range of 2 parts by weight or more to 80 parts by weight or less, especially preferably in the range of 50 parts by weight or more to 75 parts by weight or less. Especially, those nail cosmetic compositions using a silicone macromonomer having a repeating number n of a silicone unit from 10 or more to 40 or less exhibit a pleasing appearance and good glossiness after curing. The base material preferably contains, in addition to a silicone macromonomer, at least one of acryloyl morpholine, N,N-diethyl acrylamide, 2-methoxyethyl acrylate, and ethylene glycol dimethacrylate, which are copolymerization monomers. The polymerization initiator and the crosslinking agent are inferred to preferably be included in the range of 1.0 parts by weight or more to 20 parts by weight or less in the range of 2 parts by weight or more to 10 parts by weight or less, with respect to 100 parts by weight of base material.

As shown in Table 4, the resin of Experimental Example 21 did not have sufficient hardness or a pleasing appearance by curing with LED light source and also had low oxygen permeability. Furthermore, the resin of Experimental Example 22 had large dissoluble component, accounting for 19 wt % or more, and also low oxygen permeability. On the other hand, the nail cosmetic resins obtained after curing the composition described in Experimental Examples 12-20 had excellent transparency, hardness, and glossiness, a small amount of extraction of the polymerized components, and high oxygen permeability as shown in Tables 3 and 4. Specifically, the nail cosmetic resins described in Experimental Examples 12-20 showed a extraction rate of 18 wt % or less, moisture content in the range of 3 wt % or more to 20 wt % or less, and an oxygen permeability coefficient of 25 barrer or more. In general, allowing a resin with low oxygen permeability to form on a nail will cause a green nail syndrome, whereby *pseudomonas* proliferates between the nail and the resin, causing the nail to turn green. As can be seen from Experimental Examples 1-20, it is conjectured that a nail cosmetic resin with high oxygen permeability and high moisture transpirability can suppress the generation of this green nail syndrome.

TABLE 1

| Compounding Composition (parts by weight our of 100) | Ex. 1 | Ex. 2 | Ex. 3 | Ex. 4 | Ex. 5 |
|---|---|---|---|---|---|
| SiDA - B (n = 40) | 50 | 76.9 | — | — | — |
| SiDA - C (n = 20) | — | — | 50 | 76.9 | 50 |
| IBMA | 50 | 19.2 | — | — | — |
| ACMO | — | — | 50 | 19.2 | 50 |
| EDMA | — | 3.9 | — | 3.9 | — |
| TPO | 2 | 2 | 2 | 2 | 3 |
| IRG 651 | 2 | 2 | 2 | 2 | 3 |
| Features of the Composition for Nail Makeup | | | | | |
| Coatability | B | A | A | AA | A |
| Appearance after curing | A | A | A | A | A |

TABLE 2

| Compounding Compo (parts by weight out of 100) | Ex. 6 | Ex. 7 | Ex. 8 | Ex. 9 | Ex. 10 | Ex. 11 |
|---|---|---|---|---|---|---|
| SiDA - A (n = 60) | 75 | 75 | — | — | — | — |
| SiDA - B (n = 40) | — | — | 75 | 75 | — | — |
| SiDA - C (n = 20) | — | — | — | — | 75 | 75 |
| ACMO | 25 | 25 | 25 | 25 | 25 | 25 |
| TPO | 3 | 5 | 3 | 5 | 3 | 5 |
| IRG 651 | 3 | 5 | 3 | 5 | 3 | 5 |
| Features of the Composition for Nail Makeup | | | | | | |
| Coatability | A | A | A | A | A | A |
| Appearance after curing | A | A | A | A | A | A |

TABLE 3

| Compounding Composition (parts by weight out of 100) | Ex. 12 | Ex. 13 | Ex. 14 | Ex. 15 | Ex. 16 | Ex. 17 |
|---|---|---|---|---|---|---|
| SiDA - B (n = 40) | 54.5 | — | — | 10.9 | 8.2 | 5.5 |
| SiDA - C (n = 20) | — | 54.5 | — | — | — | — |
| SiDA - D (n = 10) | — | — | 54.5 | — | — | — |
| SiDA - E | — | — | — | 43.6 | 46.3 | 49 |
| ACMO | 36.4 | 36.4 | 36.4 | 36.4 | 36.4 | 36.4 |
| EDMA | 9.1 | 9.1 | 9.1 | 9.1 | 9.1 | 9.1 |
| TPO | 4.5 | 4.5 | 4.5 | 4.5 | 4.5 | 4.5 |
| IRG 651 | 4.5 | 4.5 | 4.5 | 4.5 | 4.5 | 4.5 |
| Features of the Composition for Nail Makeup | | | | | | |
| Viscosity (mPa·s) | 809 | 362 | 265 | 3990 | 7210 | 10800 |
| Coatability | A | A | B | A | AA | B |
| Features of the Resin for Nail Makeup | | | | | | |
| Appearance after curing | A | A | A | A | A | A |
| Gloss | B | A | A | A | A | AA |
| Hardness, brittleness | B | A | A | A | A | A |
| Durability | A | A | A | A | A | A |
| Extraction rate (wt % acetone · room temperature) | 10.4 | 9.5 | 8.6 | 10.7 | 10.8 | 10.7 |
| Moisture content (wt % water · room temperature) | 11.7 | 9.7 | 9.6 | 14.2 | 14.5 | 14.3 |
| Oxygen permeability (Barrer) | 220 | 121 | 33 | 181 | 169 | 180 |

TABLE 4

| Compounding Composition (parts by weight out of 100) | Ex. 18 | Ex. 19 | Ex. 20 | Ex. 21 | Ex. 22 |
|---|---|---|---|---|---|
| SiDA - C (n = 20) | 54.5 | 54.5 | 54.5 | | |
| ACMO | — | 18.2 | 18.2 | | |
| DEAA | 36.4 | 18.2 | — | | |
| 2-MTA | — | — | 18.2 | | |
| EDMA | 9.1 | 9.1 | 9.1 | | |

TABLE 4-continued

| Compounding Composition (parts by weight out of 100) | Ex. 18 | Ex. 19 | Ex. 20 | Ex. 21 | Ex. 22 |
|---|---|---|---|---|---|
| TPO | 4.5 | 4.5 | 4.5 | | |
| IRG 651 | 4.5 | 4.5 | 4.5 | | |
| Features of the Composition for Nail Makeup ||||||
| Viscosity (mPa·s) | 56 | 105 | 79 | 26400 | 53500 |
| Coatability | B | B | B | A | C |
| Features of the Resin for Nail Makeup ||||||
| Appearance after curing | A | A | A | C | A |
| Gloss | A | A | A | A | A |
| Hardness, brittleness | A | A | A | C | A |
| Durability | A | A | A | — | A |
| Extraction rate (wt % acetone · room temperature) | 8.9 | 8.7 | 8.8 | 10.0 | 19.3 |
| Moisture content (wt % water · room temperature) | 6.4 | 8.5 | 4.9 | 9.4 | 14.3 |
| Oxygen permeability (Barrer) | 92 | 96 | 128 | 15 | 21 |

TABLE 5

| Compounding Composition (parts by weight out of 100) | Ex. 23 | Ex. 24 | Ex. 25 | Ex. 26 | Ex. 27 | Ex. 28 | Ex. 29 |
|---|---|---|---|---|---|---|---|
| SiDA - B (n = 40) | — | — | — | — | 9.5 | — | — |
| SiDA - C (n = 20) | 9.1 | 9.5 | 9.5 | 9.5 | — | 27.3 | 28.6 |
| SiDA - E (n = 40) | 45.4 | 47.6 | 47.6 | 47.6 | 47.6 | 27.3 | 28.6 |
| ACMO | 36.4 | 38.1 | 38.1 | 38.1 | 38.1 | 36.3 | 38.0 |
| EDMA | 9.1 | 4.8 | — | — | 4.8 | 9.1 | 4.8 |
| TAIC | — | — | 4.8 | — | — | — | — |
| PETA | — | — | — | 4.8 | — | — | — |
| TPO | 2.7 | 2.9 | 3.0 | 3.0 | 2.9 | 2.7 | 2.8 |
| IRG 651 | 10.9 | 11.4 | 12.0 | 12.0 | 11.4 | 10.9 | 11.4 |
| Features of the Composition for Nail Makeup ||||||||
| Viscosity (mPa·s) | 5400 | 7800 | 12900 | 12200 | 9900 | 1300 | 1900 |
| Coatability | A | A | AA | AA | AA | B | B |
| Features of the Resin for Nail Makeup ||||||||
| Appearance after curing | A | A | A | A | A | A | A |
| Gloss | A | A | A | A | A | B | B |
| Hardness, brittleness | A | A | A | A | A | A | A |
| Durability | A | A | A | A | A | A | A |
| Gloss (60°) | 36 | 45 | 40 | 57 | 30 | 56 | 50 |
| Gloss (20°) | 8 | 13 | 10 | 35 | 5 | 15 | 27 |
| Moisture content (wt % water · room temperature) | 14.4 | 21.2 | 22.0 | 16.1 | 19.9 | 13.6 | 18.9 |
| Oxygen permeability (Barrer) | 148 | 159 | 151 | 156 | 173 | 212 | 139 |

TABLE 6

| Compounding Composition (parts by weight out of 100) | Ex. 30 | Ex. 31 | Ex. 32 | Ex. 33 | Ex. 34 | Ex. 35 | Ex. 36 | Ex. 37 | Ex. 38 | Ex. 39 |
|---|---|---|---|---|---|---|---|---|---|---|
| SiDA - C (n = 20) | 9.4 | 12.6 | 10.5 | 63.1 | 13.3 | 11.4 | 21.9 | 17.1 | 31.6 | — |
| SiDA - F (n = 60) | 56.1 | 50.5 | 52.6 | — | 53.3 | 55.2 | 44.7 | 49.5 | 31.6 | 63.1 |
| ACMO | 28.0 | 31.6 | 31.6 | 31.6 | 28.6 | 28.6 | 28.6 | 28.6 | 31.6 | 31.6 |
| EDMA | 6.5 | 5.3 | 5.3 | 5.3 | 4.8 | 4.8 | 4.8 | 4.8 | 5.2 | 5.3 |
| TPO | 2.8 | 3.2 | 3.2 | 3.2 | 2.9 | 2.9 | 2.9 | 2.9 | 3.2 | 3.2 |
| IRG 651 | 11.2 | 12.6 | 12.6 | 12.6 | 11.4 | 11.4 | 11.4 | 11.4 | 12.6 | 12.6 |
| Features of the Composition for Nail Makeup |||||||||||
| Viscosity (mPa·s) | 19600 | 7900 | 34200 | 700 | 13200 | 19800 | 6500 | 9300 | 3000 | 36300 |
| Coatability | A | AA | AA | B | A | A | A | A | B | C |
| Features of the Resin for Nail Makeup |||||||||||
| Appearance after curing | A | A | A | A | A | A | A | A | A | B |
| Gloss | A | A | A | A | A | A | A | A | A | A |

TABLE 6-continued

| Compounding Composition (parts by weight out of 100) | Ex. 30 | Ex. 31 | Ex. 32 | Ex. 33 | Ex. 34 | Ex. 35 | Ex. 36 | Ex. 37 | Ex. 38 | Ex. 39 |
|---|---|---|---|---|---|---|---|---|---|---|
| Hardness, brittleness | A | A | A | A | A | A | A | A | A | A |
| Durability | A | A | A | B | A | A | A | A | A | B |
| Gloss (60°) | 30 | 47 | 42 | 40 | 34 | 25 | 60 | 55 | 61 | 61 |
| Gloss (20°) | 6 | 9 | 11 | 5 | 6 | 5 | 20 | 21 | 16 | 16 |
| Moisture content (wt % water · room temperature) | 17.7 | 13.9 | 13.7 | 8.3 | 14.8 | 12.0 | 11.7 | 12.5 | 10.7 | 13.6 |
| Oxygen permeability (Barrer) | 220 | 184 | 194 | 148 | 208 | 102 | 202 | 196 | 170 | 66 |

TABLE 7

| Compounding Composition (parts by weight out of 100) | Ex. 40 | Ex. 41 | Ex. 42 | Ex. 43 | Ex. 44 | Ex. 45 |
|---|---|---|---|---|---|---|
| Ex. 21 | 95.0 | — | 50.0 | — | 50.0 | — |
| Ex. 22 | — | 95.0 | — | 50.0 | — | 50.0 |
| SiDA - F (n = 60) | 5.0 | 5.0 | — | — | — | — |
| TRIS | — | — | 50.0 | 50.0 | — | — |
| SiST | — | — | — | — | 50.0 | 50.0 |
| Features of the Composition for Nail Makeup | | | | | | |
| Viscosity (mPa · s) | Not measured due to clouding | Not measured due to clouding | Not mixed | Not mixed | Not mixed | Not mixed |
| Coatability | B | B | Not evaluated | Not evaluated. | Not evaluated | Not evaluated |
| Features of the Resin for Nail Makeup | | | | | | |
| Appearance after curing | C | C | Not evaluated | Not evaluated | Not evaluated | Not evaluated |
| Gloss | C | C | Not evaluated | Not evaluated | Not evaluated | Not evaluated |
| Hardness, brittleness | C | C | Not evaluated | Not evaluated | Not evaluated | Not evaluated |
| Durability | Not evaluated due to cloudiness | Not evaluated due to cloudiness | Not evaluated | Not evaluated | Not evaluated | Not evaluated |
| Gloss (60°) | 9 | 4 | Not evaluated | Not evaluated | Not evaluated | Not evaluated |
| Gloss (20°) | 1 | 1 | Not evaluated | Not evaluated | Not evaluated | Not evaluated |

The viscosity and coatability of the nail cosmetic compositions were confirmed, and the following items, in addition to the appearance after curing, glossiness, hardness, brittleness, durability, extraction rate, moisture content, oxygen permeability, and moisture transpirability of the nail cosmetic resins where these compositions had been cured were also evaluated.

Tables 5-7 summarize the results of evaluating the compounding ratio (wt %) of the raw material described in Experimental Examples 23-45, coatability, appearance after curing, gloss, hardness and brittleness, durability, glossiness, moisture content, and oxygen permeability coefficient. The nail cosmetic compositions described in the Experimental Examples 23-38 were found to have excellent coatability and hardness, similar to those in Experimental Examples 1-20, as shown in Tables 5 and 6. The low molecular weight crosslinking agent was found to preferably contain at least one of triallyl isocyanurate (TAIC) and pentaerythritol tetraacrylate (PETA). Furthermore, the nail cosmetic resin obtained after curing the compositions described in Experimental Examples 23-39 had excellent transparency, hardness, and gloss, a small amount of extraction of the polymerized portion, and high oxygen permeability. Specifically, the nail cosmetic resins described in Experimental Examples 23-39 had glossiness of 5 or more at a measurement angle of 20° and 25 or more at a measurement angle of 60°, moisture content in the range of 3 wt % or more to 20 wt % or less, and oxygen permeability coefficient of 25 barrer or more. The nail cosmetic resins described in Experimental Examples 15-17, 23-32, and 34-38 contained two types of silicone macromonomers having different chain length, the weight ratio of macromonomer A having short chain length in the range of 10/90 or more to 50/50 or less; or about 15/85, or about 20/80, with respect to macromonomer B having long chain length. Based on this result, it was found that it is preferable to contain two types of silicone macromonomer having different structures in a specific range. In the composition described in Experimental Example 31 containing one type of silicone macromonomer SiDA-C having small repeating number n, the composition had low viscosity and slightly decreased coatability. On the other hand, in the composition described in Experimental Example 39 containing one type of silicone macromonomer SiDA-F having higher repeating number n, the composition had high viscosity but relatively low coatability. The composition described in Experimental Example 39 had deteriorated coatability and also relatively low oxygen permeability, but excellent gloss and hardness, so that the function as nail cosmetic resin was favorable.

In Experimental Examples 40-45, which were the compositions obtained by mixing the composition of Experimental Example 21 or 22 with another silicone macromonomer, as shown in Table 7, the compositions either exhibited white turbidity or could not be mixed. The compositions described in Experimental Examples 40 and 41 that became turbid also had low coatability, poor appearance of resin after curing, low gloss and hardness, so that these compositions cannot be used as the nail cosmetic resin. The compositions described in Experimental Examples 42-45 that did not mix well were not subjected to resin evaluation.

In this way, the nail cosmetic compositions corresponding to working examples have excellent coatability and hardness, and the nail cosmetic resins obtained by curing these compositions have excellent transparency, hardness, gloss, and durability when applied to a nail. While the compositions have the same dissoluble components and moisture content as those of commercially available products, high oxygen permeability may contribute to the decrease in deterioration of nail cosmetic resin and the sensation of pressure and the suppression of the generation of a green nail syndrome.

Moisture Transpirability Comparison Study

The moisture transpirability of nail cosmetic resins was evaluated by using a VapoMeter, manufactured by Delfin Technologies Inc. Samples of the nail cosmetic composition, according to some embodiments described herein, were obtained and evaluated on a PP flat plate. Samples of commercially available gel nails and nail polishes were also prepare and subjected to testing. For gel nails, a para gel "LED para light IV" curing unit equipped with an 18 W-LED lamp (405 nm) was applied and the irradiation time was set to 1 minute. For nail polishes, two rounds of coating and drying were carried out to prepare samples. The samples were immersed in distilled water for at least 24 hours before measurement of moisture transpirability.

The samples were prepared just after removing water attached to the surface, put on the paper cloth and measured under a room temperature with no wind. Moisture transpirability was measured by pressing the VapoMeter to the surface through a standard nail adapter (95 mm). Measurements were performed twice for each material, and an average value was calculated and displayed as an integer. The oxygen permeability of the gel nails and nail polishes was also measured using the methods described above. Table 8, provided below, shows the results of the measurement of nail cosmetic resins prepared according to the present disclosure, and commercially available gel nails and nail polishes:

TABLE 8

| EXAMPLE | Oxygen Permeability (Barrer) | Moisture Transpirability (g/m$^2$ · hr.) |
| --- | --- | --- |
| Example 28 | 220 | 28 |
| Example 33 | 102 | 32 |
| Commercially Available Gel Nail Samples | | |
| Cal gel Natural Clear gel | 15 | 12 |
| para gel ART TOP GEL | 21 | 11 |

TABLE 8-continued

| EXAMPLE | Oxygen Permeability (Barrer) | Moisture Transpirability (g/m$^2$ · hr.) |
| --- | --- | --- |
| Grace Gel Clear | 5 | 8 |
| Grace Gel base | 6 | 13 |
| PREGEL excellent base | 9 | 10 |
| RAPI GEL clear base | 12 | 10 |
| VETRO color VL054 "Japanese B" | 16 | 7 |
| VETRO color VL070 "Girls talk" | N/A | 7 |
| Commercially Available Nail Polish Samples | | |
| COSME DECORTE AQMW nail enamel | 12 | 24 |
| THREE nail polish #52 "WOMAN IN ME" | 9 | 22 |
| ORLY BREATHABLE TREATMENT + COLOR "Happy&Healthy" | 10 | 26 |
| MC collection nailcolor N48 | 9 | 24 |
| Inglot O$_2$M BREATHABLE BASE | 7 | 23 |
| MAYA NAIL LACQUER | N/A | 16 |

As can be seen in Table 8, Examples 28 and 33, which include silicone macromonomers and were prepared according to the present disclosure, were found to have significantly higher oxygen permeability values than all other commercially available gel nail samples. Further, Examples 28 and 33 were found to have higher moisture transpirability values than all other commercially available gel nail samples. Surprisingly, it was found that the moisture transpirability of Examples 28 and 33 were higher than even the nail polish samples, which are generally considered to have very high oxygen permeability and moisture transpirability. Thus, the unexpectedly high oxygen permeability and moisture transpirability of the samples prepared according to the present disclosure may contribute to the decrease in deterioration of nail cosmetic resin, increase nail health, and reduce the likelihood of bacterial growth that results in green nail syndrome.

As shown in Table 8 above the present formulations provide increased moisture transpirability, particularly when compared to other gel nail samples, and an overall increased oxygen permeability. Specifically, the present formulations provide for moisture transpirability preferably greater than 28 g/m$^2$·hr, in some embodiments greater than 15 g/m$^2$·hr and oxygen permeability preferably greater than 100 barrer, greater than 75 barrer, in some embodiments greater than 50 barrer, in other embodiments greater than 25 barrer, and in yet other embodiments greater than 21 barrer.

Unless otherwise indicated, all numbers or expressions, such as those expressing dimensions, physical characteristics, etc., used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

In addition, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

The invention claimed is:

1. A gel nail cosmetic composition, comprising:
   a photocurable material configured to be applied to the surface of a nail, wherein the gel nail cosmetic composition, when cured, has a moisture transpirability of greater than about 15 g/m²·hr and has an oxygen permeability coefficient of at least 25 barrer, and a surface gloss of the cured nail cosmetic composition, as measured by a gloss meter, is at least 5 at 20° or at least 25 at 60°; and
   a base material of the photocurable material including:
     a silicone macromonomer having at least two polymerizable functional groups;
     at least one of acryloyl morpholine, N,N-diethylacrylamide, and 2-methoxyethyl acrylate; and
     a polymerization initiator configured to selectively initiate polymerization of the silicone macromonomer, wherein the silicone macromonomer has a structure according to the chemical formula:

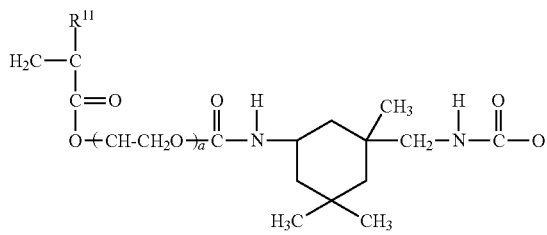

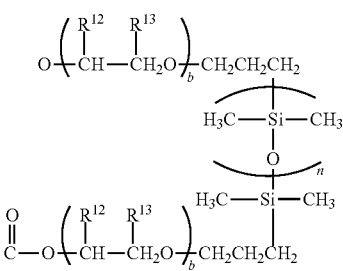

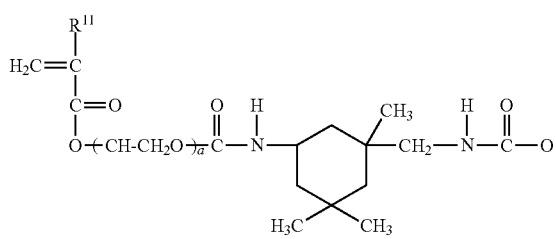

wherein $R^{11}$, $R^{12}$, and $R^{13}$ are each a hydrogen or an alkyl group having 3 or fewer carbon atoms;
   wherein n is from 10 to 60; and
   wherein a and b are each between 1 and 15.

2. The gel nail cosmetic composition of claim 1, wherein the moisture transpirability of the cured gel nail cosmetic composition is greater than about 28 g/m²·hr.

3. The gel nail cosmetic composition of claim 1, wherein the silicone macromonomer comprises at least two chemically distinct silicone macromonomers.

4. The gel nail cosmetic composition of claim 3, wherein the at least two chemically distinct silicone macromonomers comprise a first silicone macromonomer having a first structure, and a second silicone macromonomer having a second structure;
   wherein a chain length of the second structure is longer than a chain length of the first structure; and
   wherein the second silicone macromonomer is included in a weight ratio greater than or equal to that of the first silicone macromonomer.

5. The gel nail cosmetic composition of claim 3, comprising:
   a first silicone macromonomer, wherein a=b=1; and
   a second silicone macromonomer, wherein a≥1 and b>1;
   wherein a mass ratio of the first silicone macromonomer with respect to the second silicone macromonomer is from about 10/90 to about 50/50.

6. The gel nail cosmetic composition of claim 1, wherein the silicone macromonomer comprises from about 2 weight percent to about 80 weight percent of the base material.

7. The gel nail cosmetic composition of claim 6, wherein the polymerization initiator comprises from about 2 weight percent to about 15 weight percent of the base material.

8. The gel nail cosmetic composition of claim 1, further comprising:
   a crosslinking agent, wherein the crosslinking agent includes at least one of a bifunctional crosslinking agent, a trifunctional crosslinking agent, or a tetrafunctional crosslinking agent.

9. The gel nail cosmetic composition of claim 1, wherein the gel nail cosmetic composition has a viscosity of from about 50 mPa·s to about 38,000 mPa·s as measured at 20° using a rotational viscometer.

10. A nail cosmetic composition configured to be applied to the surface of a nail and cured, comprising a photocurable material comprising a polymer formed from a silicone macromonomer having at least two polymerizable functional groups;
   wherein the nail cosmetic composition, when cured, has a moisture transpirability of greater than about 15 g/m²·hr and an oxygen permeability greater than about 21 barrer, and a surface gloss of the cured nail cosmetic composition, as measured by a gloss meter, at least 5 at 20° or at least 25 at 60°; and
   at least one of acryloyl morpholine, N,N-diethylacrylamide, and 2-methoxyethyl acrylate and a polymerization initiator configured to selectively initiate polymerization of the silicone macromonomer, wherein the silicone macromonomer has a structure according to the chemical formula:

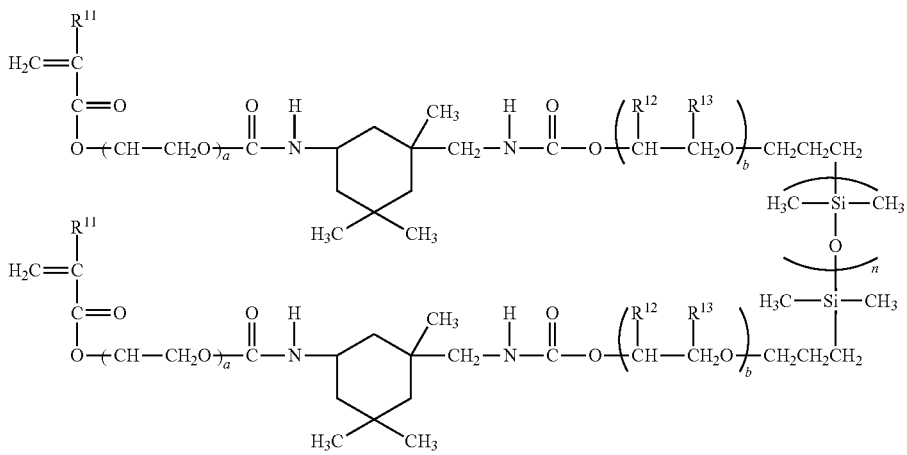

wherein $R^{11}$, $R^{12}$, and $R^{13}$ are each a hydrogen or an alkyl group having 3 or fewer carbon atoms;
wherein n is from 10 to 60; and
wherein a and b are each between 1 and 15.

11. The nail cosmetic composition of claim 10, wherein the oxygen permeability coefficient of the nail cosmetic resin is at least 25 barrer, and a moisture content of from about 3 weight percent to about 20 weight percent.

12. The nail cosmetic composition of claim 10, wherein the moisture transpirability of the cured nail cosmetic composition is greater than about 25 g/m²·hr.

13. A gel nail cosmetic composition configured to be applied to the surface of a nail and photocured, wherein the cured gel nail cosmetic composition has a moisture transpirability of greater than about 25 g/m²·hr, and an oxygen permeability greater than about 21 barrer, and a surface gloss of the cured nail cosmetic composition, as measured by a gloss meter, at least 5 at 20° or at least 25 at 60°, wherein the gel nail cosmetic composition comprises a base material including:
    a silicone macromonomer having at least two polymerizable functional groups;
    at least one of acryloyl morpholine, N,N-diethylacrylamide, and 2-methoxyethyl acrylate; and
    a polymerization initiator configured to selectively initiate polymerization of the silicone macromonomer, wherein the silicone macromonomer has a structure according to the chemical formula:

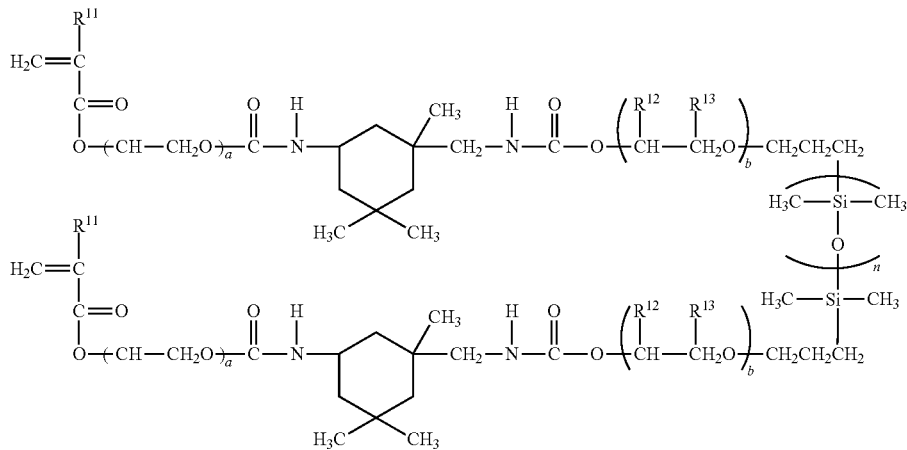

wherein $R^{11}$, $R^{12}$, and $R^{13}$ are each a hydrogen or an alkyl group having 3 or fewer carbon atoms;
wherein n is from 10 to 60; and
wherein a and b are each between 1 and 15.

14. The gel nail cosmetic composition of claim 13, wherein the oxygen permeability of the cured gel nail cosmetic composition is greater than about 25 barrer.

15. The gel nail cosmetic composition of claim 13, wherein the oxygen permeability of the cured gel nail cosmetic composition is greater than about 50 barrer.

16. The gel nail cosmetic composition of claim 13, wherein the oxygen permeability of the cured gel nail cosmetic is greater than about 75 barrer.

17. The gel nail cosmetic composition of claim 13, wherein the oxygen permeability of the cured gel nail cosmetic composition is greater than about 100 barrer.

18. A photocured nail cosmetic resin for nail cosmetics, comprising:
a silicone unit polymerized by a silicone macromonomer as a base material;
wherein the silicone macromonomer has two or more polymerizable functional groups and an oxygen permeability coefficient of the cured nail cosmetic resin is at least 25 barrer, and a surface gloss of the cured nail cosmetic resin, as measured by a gloss meter, at least 5 at 20° or at least 25 at 60°;
the base material further includes at least one of acryloyl morpholine, N,N-diethylacrylamide, and 2-methoxyethyl acrylate; and
a polymerization initiator configured to selectively initiate polymerization of the silicone macromonomer, wherein the silicone macromonomer has a structure according to the chemical formula:

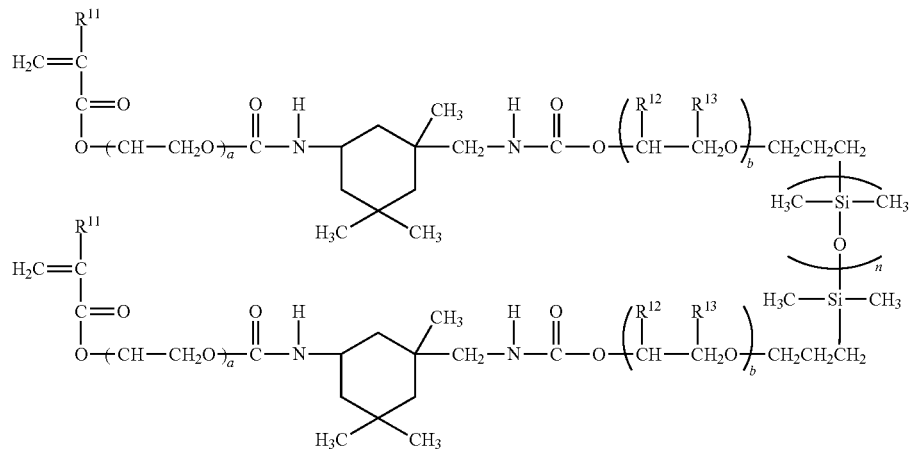

wherein $R^{11}$, $R^{12}$, and $R^{13}$ are each a hydrogen or an alkyl group having 3 or fewer carbon atoms;
wherein n is from 10 to 60; and
wherein a and b are each between 1 and 15.

* * * * *